United States Patent [19]

Tervamäki et al.

[11] Patent Number: 4,690,005
[45] Date of Patent: Sep. 1, 1987

[54] DILUTING DOSAGE DEVICE

[75] Inventors: Jukka Tervamäki, Helsinki; Kari Järvimäki, Espoo, both of Finland

[73] Assignee: Labstystems Oy, Helsinki, Finland

[21] Appl. No.: 794,104

[22] Filed: Nov. 1, 1985

[30] Foreign Application Priority Data

Nov. 2, 1984 [FI] Finland ................................ 844320

[51] Int. Cl.⁴ .......................... B01L 3/02; G01N 1/14
[52] U.S. Cl. .............................. 73/864.12; 73/864.17; 73/864.18
[58] Field of Search .......... 73/864.01, 864.11, 864.12, 73/864.13, 864.16, 864.17, 864.18, 864.22, 864.24, 864.25; 436/179

[56] References Cited

U.S. PATENT DOCUMENTS

| 3,273,402 | 9/1966 | Farr | 73/864.12 |
|---|---|---|---|
| 3,656,351 | 4/1972 | Raczak | 73/864.18 |
| 3,810,391 | 5/1974 | Suovaniemi | 73/864.18 |
| 3,955,930 | 5/1976 | Shapiro | 73/864.12 |
| 4,207,074 | 6/1980 | Suzuki | 73/864.12 |
| 4,257,208 | 3/1981 | Pepicell et al. | 73/864.17 |
| 4,327,595 | 5/1982 | Schultz | 73/864.12 |
| 4,362,063 | 12/1982 | d'Autry | 73/864.13 |
| 4,466,298 | 8/1984 | Tervamaki et al. | 73/864.18 |
| 4,501,163 | 2/1985 | MacDermott et al. | 73/864.13 |

Primary Examiner—Stewart J. Levy
Assistant Examiner—Robert R. Raevis
Attorney, Agent, or Firm—Hopgood, Calimafde, Kalil, Blaustein & Judlowe

[57] ABSTRACT

Diluting dosage device, in which there is a dilution-liquid cylinder (20), a sample cylinder (30), a press knob (2), and a blocking valve (21). When the knob is depressed, the blocking valve is closed and the pistons (16 and 15) in the cylinders move rearwards, whereat dilution liquid flows into the dilution-liquid duct (2), and a certain quantity of sample into the sample duct (23). When the press knob is returned, the blocking valve is opened and the pistons push the sucked sample and a certain quantity of the dilution liquid out through the tip (7).

9 Claims, 7 Drawing Figures

DILUTING DOSAGE DEVICE

The present invention is concerned with a dosage device by means of which it is possible to take a sample out of a liquid, to mix the sample into a diluting liquid, e.g. a reagent, in a precise proportion, and to dose the mixture into another vessel, e.g. a test tube or measurement vessel.

When liquid samples are treated in laboratories, they must often be diluted or mixed in a certain proportion. Traditionally, this has been done, e.g., by pipetting the desired quantities of liquids separately into the same vessel. This is, however, quite slow, in particular when large numbers of samples are treated.

In order to facilitate the pipetting, different diluting dosage devices have been developed. Several devices, however, still involve the drawback that one dilution requires several working steps, or that it is not possible to adjust the quantities of the liquids to be mixed.

From the U.S. Pat. No. 3,955,930, a diluting dosage device is known in which the volumes of the liquids to be dosed can be adjusted. By means of this device, it is possible, by one lifting movement, to suck a desired volume of diluent out of a vessel attached to the device into a diluent cylinder as well as, at the same time, through an open tip, to suck the desired volume of the sample into the sample cylinder. The cylinders can be emptied through the said open tip by one pressing movement. When this device is used, two working movements are required. The stroke length of the piston of the reagent cylinder cannot be adjusted longer than the stroke length of the piston of the diluent cylinder, which restricts the available dilution ratios. Moreover, the device involves the technical problem that the rod of the reagent piston is connected with the rod of the diluent piston by means of a yielding joint. Since the cylinders are supposed to be emptied by pressing a knob placed at the end of the rod of the diluent piston, the said joint may yield if the resisting force of the liquid is sufficiently high. In such a case, all the reagent is not removed out of the device.

From the published Patent Applications DE No. 2,624,899 and DE No. 2,649,014 (correspond to the publication GB 1,558,931 A) a similar two-cylinder diluting dosage device is known. In that device, a mantle is attached to the piston rod of each cylinder, which said mantle surrounds the cylinder. The mantle is provided with a limiter, whose location in the vertical direction can be shifted. At the top end of the cylinder, there is a projection meeting the limiter. In this way, the upper position of the piston is adjustable. Between the cylinders, there is an actuator supported on a guide rail parallel to the cylinders, which said actuator is provided with grasping members resting against the said displaceable limiters and placed below the said limiters. In this device as well, one dilution requires both a lifting movement and a lowering movement.

It is a common matter of additional inconvenience in the devices cited above that two hands are required for their operation unless they are used as supported on a table. It is a technical deficiency of these devices that, during the suction step, the valve between the cylinders may open itself if the pressure in the sample cylinder is to a sufficient extent lower than the pressure in the diluent cylinder. In the above devices, the suction length of the pistons cannot be read very accurately either, and the devices have no possibility of calibration at all.

The object of the present invention is, above all, to provide a diluting dosage device usable freely by one hand. It is an additional objective to provide a device in which the dosage volumes of the diluent and of the sample can be adjusted independently from each other.

The device in accordance with the invention is provided with a dilution-liquid cylinder and with a sample cylinder, each of the said cylinders being provided with a piston for the sucking of liquid. The dilution-liquid cylinder communicates with the dilution-liquid container via a duct, which is provided with an intake valve. The sample cylinder communicates with a dosage tip via a sample duct. Moreover, between the cylinders, there is a connecting duct, and therein a blocking valve, which is opened when there is a positive pressure in the dilution-liquid container.

The piston rod of each cylinder is provided with a spring, which presses the piston towards the open end of the cylinder. The device is further provided with a filling lever; when the lever is pressed, both pistons move backwards against the spring force. A preferred embodiment further includes an adjustment limiter, preferably separately for each cylinder, which determines at what stage of the movement of the press lever the piston starts moving. The blocking valve is preferably such a diaphragm valve upon which a negative pressure in any one of the cylinders has a closing effect. The device has a handle, preferably shaped as fitting in the hand, in which handle the filling lever can be pressed by the finger. In view of increasing the accuracy, the volume display scales may be made calibrable.

The invention will be illustrated in more detail by means of the accompanying drawings, in which.

Figure 1:
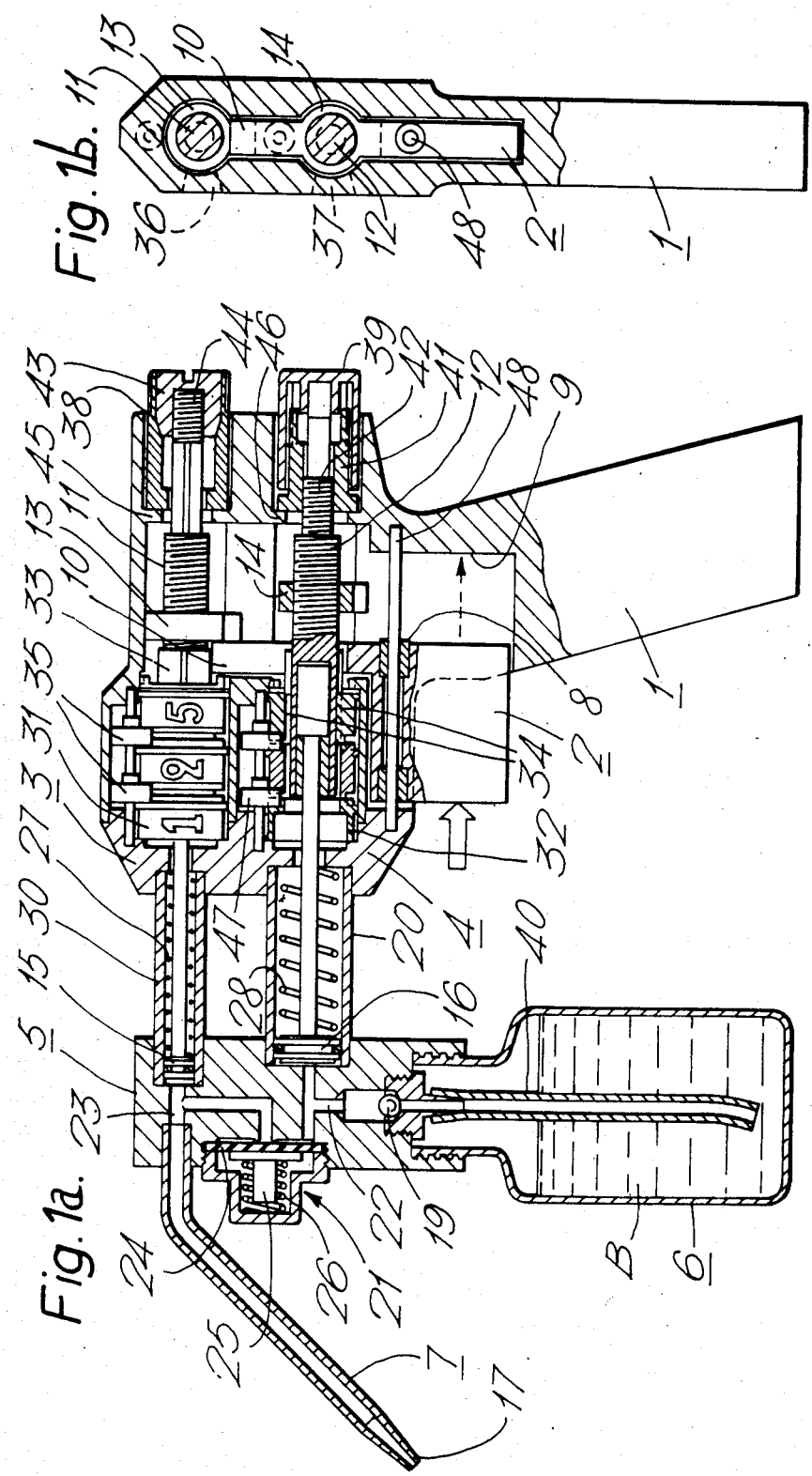
FIG. 1a is a side elevational view of one embodiment of the invention partially sectioned longitudinally.
FIG. 1b is an end elevational view of the right end of the embodiment of FIG. 1a, in partial transverse section.

Throughout the figures of the drawings similar or analogous parts are designated by the same reference numeral followed by a prime or double prime, where appropriate, to distinguish between the several embodiments. Unless the operation or function is different, the primed components will not be separately described in order to avoid unnecessary repetition.

Figure 2:
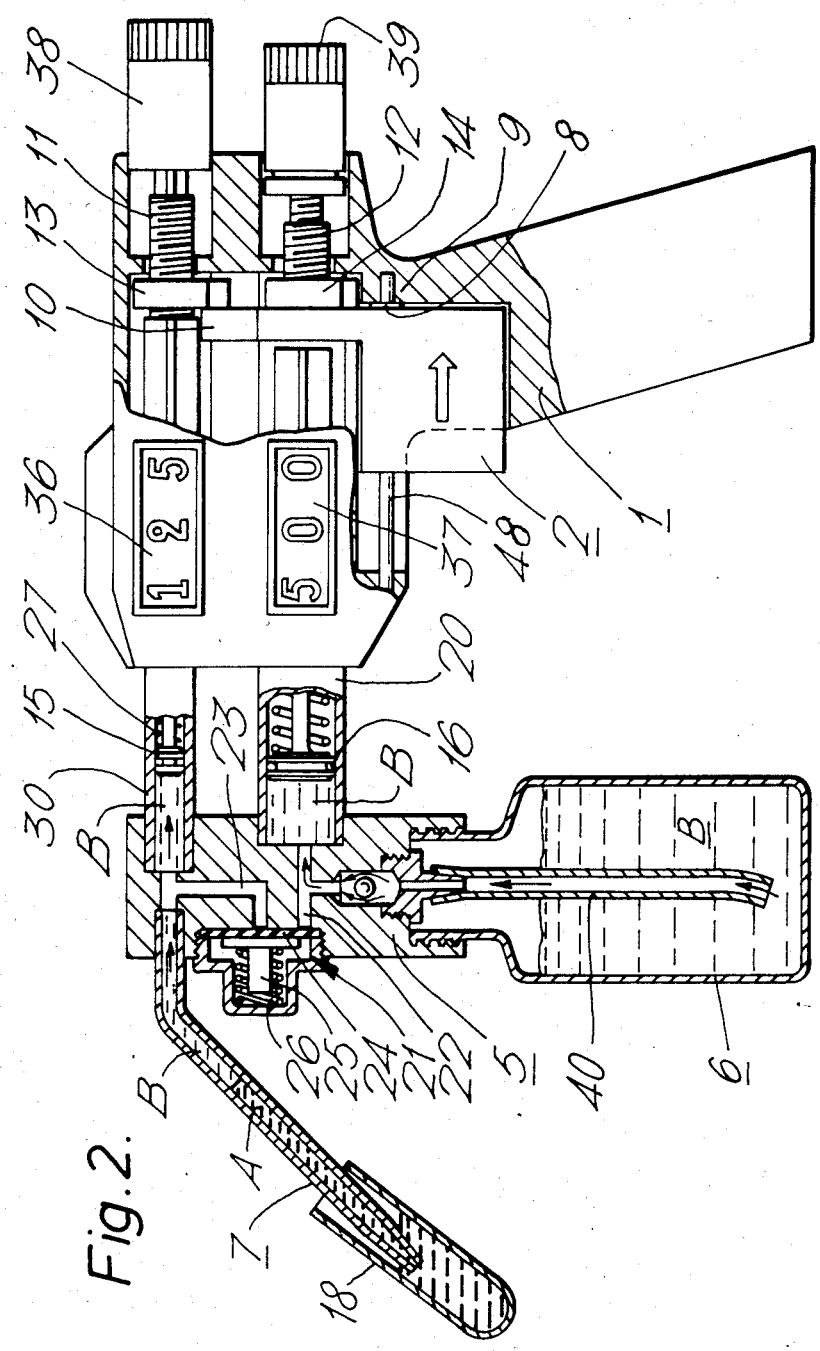
FIG. 2 is a side elevational view of the embodiment of FIG. 1a with somewhat less sectioning and showing the device in operation.
Figure 3:
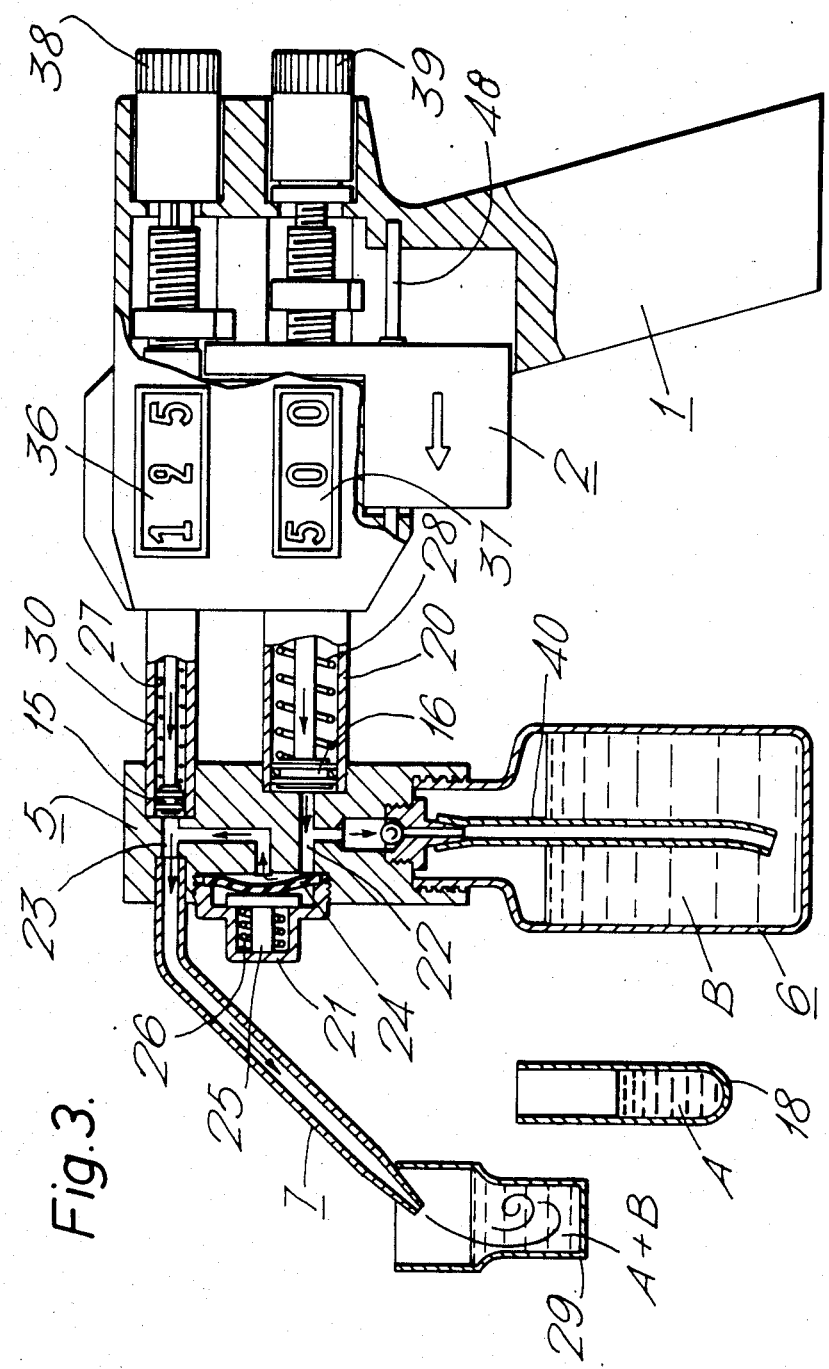
FIG. 3 is a view similar to FIG. 2 showing the same embodiment and a subsequent operation thereof.

The diluting dosage device shown in FIGS. 1 to 3 consists of the following main parts: handle 1, operating lever 2, adjustable measurement and dosage part 3 for liquid A, adjustable measurement and dosage part 4 for liquid B, valve unit 5, and storage bottle 6 for liquid B, as well as a dosage tip 7. FIGS. 1a and 1b illustrate the construction of the interior parts of the diluting dosage device, FIG. 2 the operation at the suction stage, and FIG. 3 the operation at the dosage stage.

The liquid A is sucked into the dosage tip 7 through the mouth 17, through which the liquids A and B are also removed. The other end of the dosage tip 7 is connected to the tube 23 in the valve unit 5.

The liquid B is sucked into the device out of the bottle 6 via the hose 40 into the tube 22 placed in the valve unit 5. Between the hose 40 and the tube 22, there is a suction valve 19, which prevents access of the liquid B from the valve unit 5 back into the bottle 6. The side brances in the tubes 23 and 22 pass into the chamber of the valve 21, wherein a diaphragm 24 is pressed against their mouths by the force of the spring 26 and by the intermediate of the piston 25. During the suction stage, there is a negative pressure in the tubes 22 and 23, so that the diaphragm 24 closes the mouths of the tubes 22 and 23 tightly, being aided by the piston 25 and by the spring 26, and no movement of liquid A or B can take place through the valve 21 during the suction stage.

The other end of the tube 22 communciates with the cylinder 20 in the dosage part 4 for the liquid B, which said cylinder 20 is provided with a tightly sealed piston 16 and with a spring 28, which presses the piston towards the end of the tube 22 opening into the cylinder 20. On the adjustment shaft 12 of the piston 16, which is placed in the handle 1, a threaded nut 14 is fitted so that it cannot revolve relative the handle 1, but that it can move in the longitudinal direction along the adjustment shaft 12 when the adjustment shaft is rotated. Moreover, on the adjustment shaft 12, above the adjustment threading, there is a separate, smaller calibration threading 42, which is related to a calibration nut 41. At the end of the adjustment shaft 12, there is a detachable adjustment knob 39, which is fitted non-rotably relative the adjustment shaft. By means of the adjustment knob 39, it is, thus, possible to rotate the adjustment shaft 12, whereby the nut 14 is shifted along the shaft accordingly. When the adjustment knob 39 is pulled out, it is possible to rotate the calibration nut 41 and thereby to set the front limit of the movement of the piston exactly at the desired position.

In a corresponding way, as the tube 22 communicates with the dosage part 4 for the liquid B, the tube 23 communicates with the dosage part 3 for the liquid A, which said part 3, in a corresponding way, comprises a cylinder 30, a piston 15, a spring 27, and adjustment shaft 11, a threaded nut 13, and an adjustment knob 38. The calibration is arranged by means of a calibration nut 43 and a calibration threading 44.

Moreover, each dosage part 3 and 4 is connected with a mechanism fitted in the handle 1, in which the adjustment shafts 11 and 12 rotate series of numbered rings 31 and 32 by means of keys 33 and 34 and cogwheels 35 and 47. In this way, the adjustment volume of each liquid unit 3 and 4 can be displayed in the desired way in the windows 36 and 37 numerically, e.g. at intervals of 1 $\mu$l or 0.1 $\mu$l. One volume display system of this sort in connection with pipettes is described in more detail, e.g., in the Finnish Pat. No. 64,752 (corresponds to EP No. 112,887).

The operating lever 2 is fitted so that it moves in the handle 1 guided by the rail 48 as parallel to the adjustment shafts 11 and 12. The operating lever 2 is provided with a projection 10, which is fitted so as to rest against the nuts 13 and 14 from the side of the pistons 15 and 16. The limiter 8 on the operating lever 2 and the corresponding limiter face 9 on the handle determine the rear limit of the movement of the lever 2.

The front limit of the movement of the pistons 15 and 16 is determined by the partition walls 45 and 46 provided in the handle 1, the calibration nut 41 or the adjustment knob 38, respectively, meeting the said partition walls.

When the operating lever 2 moves rearwards (FIG. 2), the projection 10 on the lever 2 engages, during the movement, the nuts 13 and 14, fitted on the adjustment shafts 11 and 12 both for the liquid A and for the liquid B, whereby, along with the movement of the lever 2, also the nuts 13 and 14, the adjustment shafts 11 and 12, and the pistons 15 and 16 attached to them start moving rearwards in the cylinders 20 and 30 until the limiter 8 on the lever 2 meets the face 9. Thereat, liquid A, e.g. sample from the test tube 18, flows through the mouth 17 into the dosage tip 7 and, at the same time, liquid B, e.g. reagent, flows from the bottle 6 through the suction valve 19 into the cylinder 20.

The return movement of the pistons 15 and 16 to their initial positions (FIG. 3) takes place by means of the springs 27 and 28, which were tensioned during the pulling/suction movement. When the lever 2 is allowed to return to its initial position, the piston 15 in the cylinder 30 pushes the liquid A out of the dosage tip 7 through its mouth 17 into the desired vessel, e.g. a set of measurement cuvettes 29, and, at the same time, when the piston 16 starts moving in the cylinder 20 towards the initial position, the positive pressure produced closes the suction valve 19 and opens the exhaust valve 21 diaphragm 24, whereat the liquid B starts flowing out of the tube 22 into the tube 23 and from there through the dosage tip 7 out into the same vessel 29 into the liquid A, being mixed with the liquid A completely. At the same time, the liquid B washes the sample tip 7 clean of the liquid A. The washing takes place best if the liquid quantity B has been chosen considerably larger than the liquid quantity A, e.g. B:A=10:1 or 100:1.

Before the diluting dosage described above is started, the liquid spaces in the device (tubes, valves, cylinders, and the tip) must be filled with the liquid B, i.e. the device must be "bled". This takes place by moving the lever 2 back and forth several times, whereby the liquid B fills all the ducts and removes the air. The excess liquid flowing out of the tip 7 is preferably passed by means of a hose back into the bottle 6 (not shown in the drawings).

The adjustment mechanisms and the volume display systems of both of the liquid measurement and dosage parts can be made as of a construction corresponding to the operation and adjustment mechanisms of ordinary manually operated pipettes, known in prior art, e.g. in the ways described in the Finnish Pat. Nos. 64,752, 57,542, 57,543 (correspond to the publications EP No. 112,887, GB No. 2,021,972, and GB No. 2,022,453).

The valve system 5 in accordance with the figures, wherein the negative pressure in the tubes 22 and 23 during the suction stage acts on the same side of the valve diaphragm 24, is particularly favourable, because in this way opening of the valve during the suction stage is prevented even if there were a considerable difference in pressure between the tubes.

Figure 4:
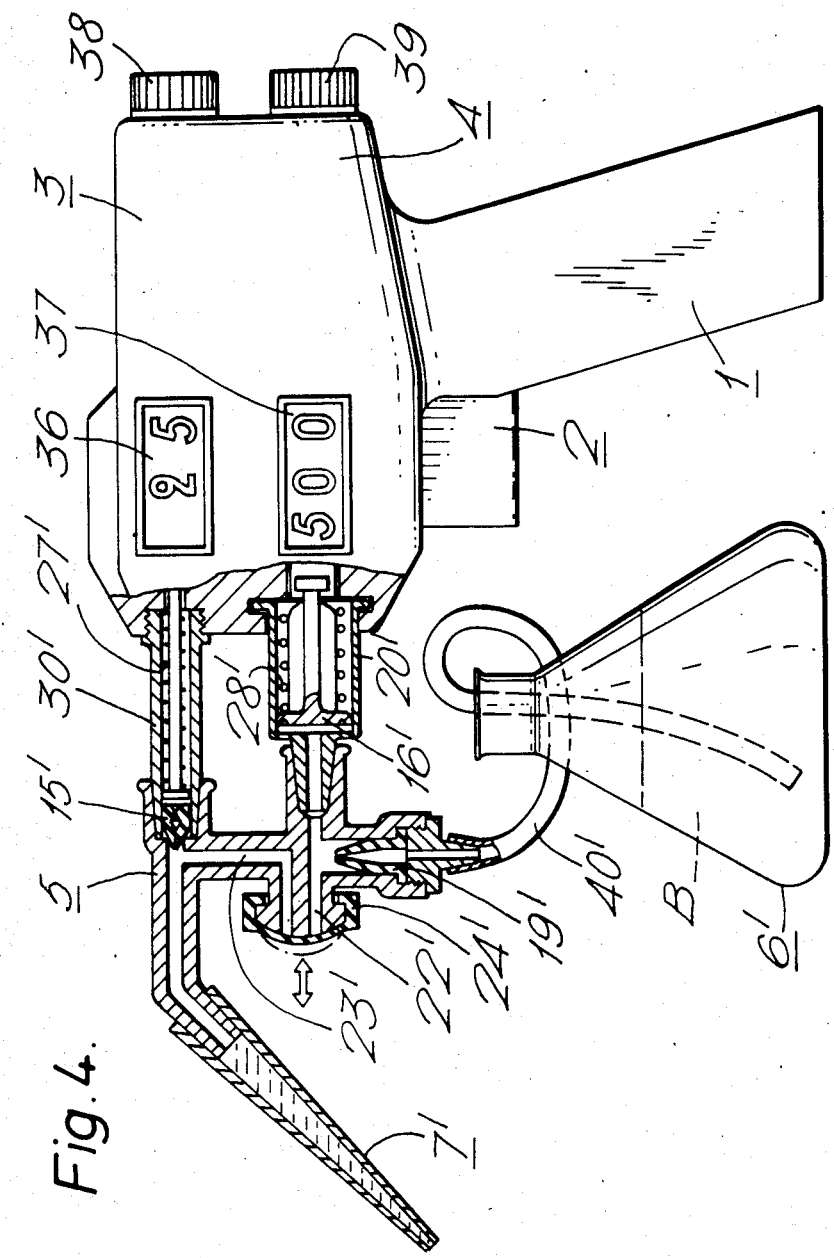
FIG. 4 is a side elevational view of another embodiment of the invention in partial longitudinal section.
Figure 5A:
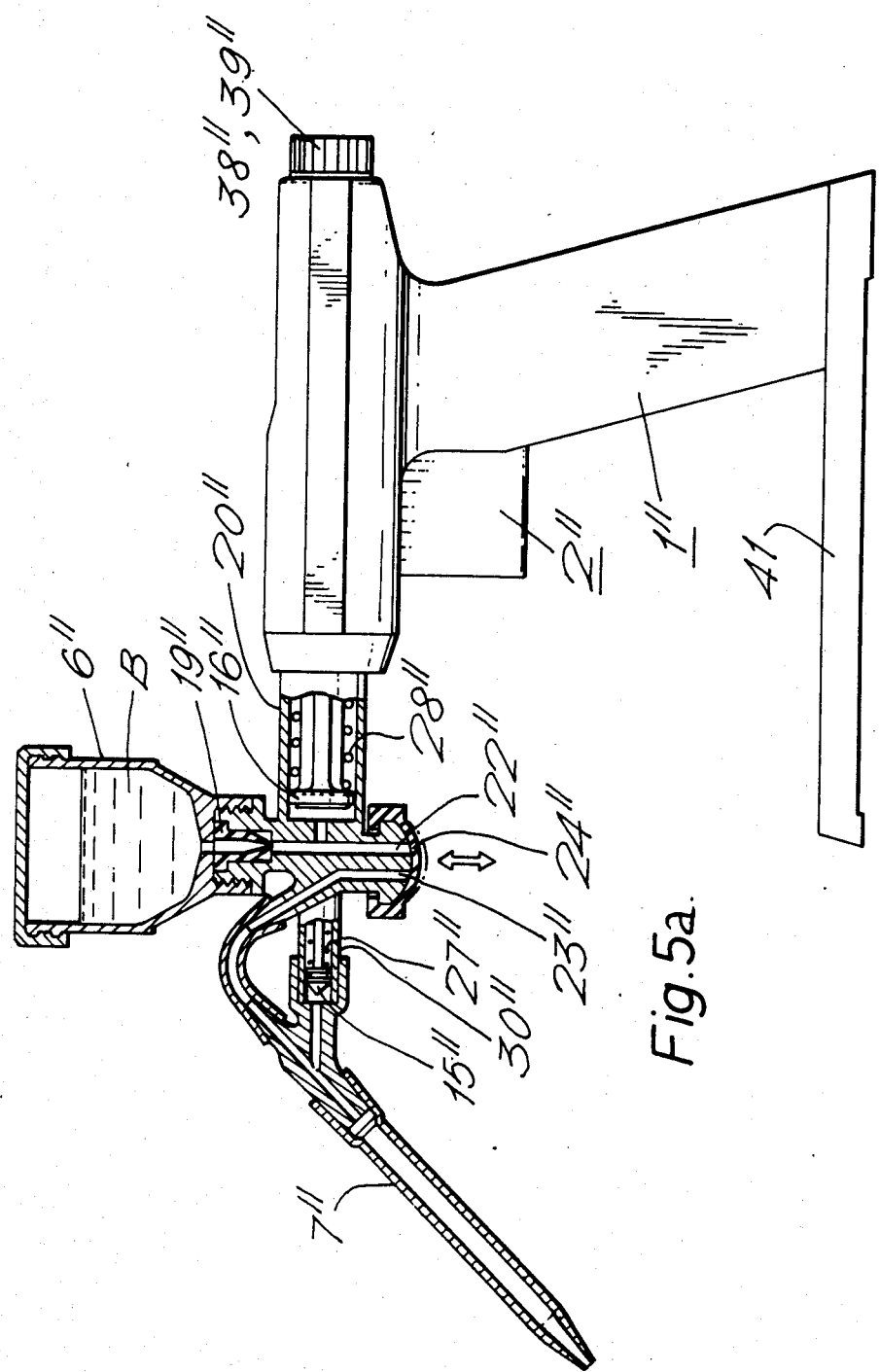
FIG. 5a is a view similar to FIG. 4 showing a further embodiment of the invention.
Figure 5B:
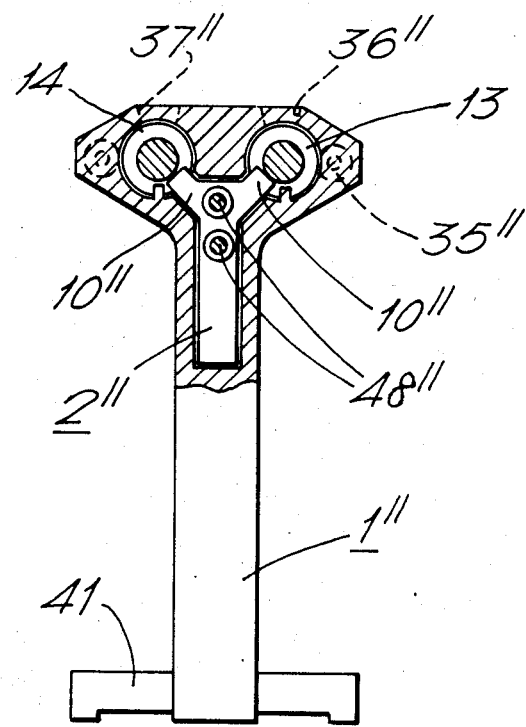
FIG. 5b is an end elevational view of the right end of the embodiment of FIG. 5a, in partial transverse section.

In the devices in accordance with FIGS. 4 and 5, the blocking valves between the liquid units consist of resilient diaphragms 24' and 24", which may be, e.g., of silicon rubber. When the pistons 16' and 16" are returned, being pressed by the springs 28' and 28", a positive pressure is formed in the tubes 22' and 22". Thereat the diaphragms 24' and 24" yield, and the liquid B flows into the tubes 23' and 23".

The suction valve for the liquid B may be, e.g., a spherical valve 19 (FIG. 1a) or a flap valve 19', 19" (FIGS. 4 and 5).

In accordance with FIG. 5, the device may preferably have a 3-foot base 41, on which it stands when the device is not being used or when liquid is being added into the bottle 6".

The liquid units may, of course, be attached to the handle either one above the other (FIGS. 1 to 4), side by side (FIG. 5), or as a group of another sort. In accordance with FIG. 4, the bottle 6' may also be separate from the device, in which case only the intake hose 40' is connected with the valve unit 5', or the bottle 6" may be placed above the valve unit 5", as is shown in FIG. 5a. In principle, there may also be a higher number of dosage units.

Also, the other details, such as the shape of the valve unit and its mode of attachment to the handle, the sealing of the pistons in their cylinders, the shape and location of the springs, the shape of the handle, and the location of the dosage lever and of the adjustment units may show variation to a considerable extent. In FIGS. 1 to 5, only some embodiments are illustrated that are found advantageous.

What is claimed is:

1. Diluting dosage device for the dilution and dosage of liquids, which said device includes a handle (1), in which there is a dilution-liquid cylinder (20) open at one end, and in said cylinder a sealed first piston (16) provided with a first piston rod (12), said first piston being connected with a first spring (28), which presses the first piston towards the open end of the dilution-liquid cylinder; in which said handle there is further a sample cylinder (30) open at one end and therein correspondingly a second piston (15) provided with a second rod (11), the second piston being connected with a second spring (27), which presses the second piston towards the open end of the sample cylinder, in which said handle there is further an operating knob (2) engaging the said piston rods for pulling said pistons apart from the open ends of their cylinders; and a valve unit (5), in which there is a dilution-liquid duct (22) provided with a side branch, one end of the said dilution-liquid duct (22) communicating with the open end of said dilution-liquid cylinder and the other end of the said dilution-liquid duct (22) being provided with a suction valve (19), which valve is open when there is a negative pressure in said dilution-liquid duct, and closed when there is a positive pressure in said dilution-liquid duct, in which said valve unit there is further a sample duct (23) provided with a side branch, one end of the said sample duct (23) communicating with the open end of said sample cylinder and the other end of the said sample duct (23) being open, and in which said valve unit the side branch of said dilution-liquid duct and the side branch of said sample duct communicate with each other via a blocking valve (21), which blocking valve is closed when there is a negative pressure in said dilution-liquid duct, and open when there is a positive pressure in said dilution-liquid duct.

2. Diluting dosage device as claimed in claim 1, characterized in that an adjustable movement limiting member is disposed in coupled relationship between said handle and one of said pistons for adjustably determining one extreme limit of movement of said one piston.

3. Diluting dosage device as claimed in claim 2, characterized in that said movement limiting member is a nut threadedly mounted on the rod provided for said one piston, means within said handle for engaging said nut and preventing said nut from rotating relative to said handle, and said operating knob includes an arm mounted to travel along a path containing said nut for engaging said nut to effect said pulling of said one piston apart from the open end of its cylinder.

4. Diluting dosage device as claimed in claim 2, characterized in that a second adjustable movement limiting member is disposed in coupled relationship between said handle and said one of said pistons for adjustably determining another extreme limit of movement of said one piston opposite to said one extreme limit of movement.

5. Diluting dosage device as claimed in claim 1, characterized in that said side branches each has a mouth at a respective branch end that communicates with said blocking valve, and said blocking valve is provided with a diaphragm (24, 24', 24") which sealingly engages said mouths of said side branches in the absence of positive pressure in said dilution-liquid duct.

6. Diluting dosage device as claimed in claim 5, characterized in that the diaphragm of the blocking valve is a resilient diaphragm (24',24") tensioned onto the mouths of the side branches.

7. Diluting dosage device as claimed in claim 1, characterized in that the device is provided with a stand (41) on which the device stands so that the cylinders and positioned substantially horizontally.

8. Diluting dosage device as claimed in claim 7, characterized in that the suction valve is connected with a liquid container (6") placed above the valve unit.

9. Diluting dosage device as claimed in claim 1, characterized in that the handle (1) is provided with a grip, and said operating knob comprises a finger operable member mounted in said grip for movement under finger pressure.

* * * * *